United States Patent
Tsion

(10) Patent No.: US 10,668,121 B2
(45) Date of Patent: *Jun. 2, 2020

(54) DIETARY SUPPLEMENTS FOR TREATING ADHD AND RELATED DISORDERS

(71) Applicant: CARE 4 STYLE LTD, Jerusalem (IL)

(72) Inventor: Yeheskel Tsion, Jerusalem (IL)

( * ) Notice: Subject to any disclaimer, the term of this patent is extended or adjusted under 35 U.S.C. 154(b) by 118 days.

This patent is subject to a terminal disclaimer.

(21) Appl. No.: 16/010,527

(22) Filed: Jun. 18, 2018

(65) Prior Publication Data
US 2018/0296622 A1 Oct. 18, 2018

Related U.S. Application Data

(63) Continuation of application No. 15/023,390, filed as application No. PCT/IL2014/050828 on Sep. 16, 2014, now Pat. No. 9,999,644.

(60) Provisional application No. 61/880,185, filed on Sep. 20, 2013, provisional application No. 62/021,225, filed on Jul. 7, 2014.

(51) Int. Cl.
| | |
|---|---|
| *A61K 36/00* | (2006.01) |
| *A61K 36/537* | (2006.01) |
| *A61K 36/84* | (2006.01) |
| *A61K 31/593* | (2006.01) |
| *A61K 33/06* | (2006.01) |
| *A61K 36/16* | (2006.01) |
| *A61K 31/202* | (2006.01) |
| *A61K 31/355* | (2006.01) |
| *A61K 31/4415* | (2006.01) |
| *A61K 9/00* | (2006.01) |
| *A61K 9/20* | (2006.01) |
| *A61K 9/48* | (2006.01) |
| *A61K 31/194* | (2006.01) |
| *A61K 33/10* | (2006.01) |
| *A61K 33/26* | (2006.01) |
| *A61K 36/35* | (2006.01) |
| *A61K 9/08* | (2006.01) |

(52) U.S. Cl.
CPC .......... *A61K 36/537* (2013.01); *A61K 9/0053* (2013.01); *A61K 9/20* (2013.01); *A61K 9/48* (2013.01); *A61K 31/194* (2013.01); *A61K 31/202* (2013.01); *A61K 31/355* (2013.01); *A61K 31/4415* (2013.01); *A61K 31/593* (2013.01); *A61K 33/06* (2013.01); *A61K 33/10* (2013.01); *A61K 33/26* (2013.01); *A61K 36/16* (2013.01); *A61K 36/35* (2013.01); *A61K 36/84* (2013.01); *A61K 9/08* (2013.01); *A61K 9/4841* (2013.01)

(58) Field of Classification Search
CPC ...................................................... A61K 36/00
USPC ........................................................ 424/725
See application file for complete search history.

(56) References Cited

U.S. PATENT DOCUMENTS 8,183,227 B1    5/2012  Perrin et al.

FOREIGN PATENT DOCUMENTS

| JP | 10298070 | * 11/1998 |
|---|---|---|
| WO | 9529668 | 11/1995 |
| WO | 2009155585 | 12/2009 |

OTHER PUBLICATIONS

Benor, D. J., & IJHC, A. (2006). "Complementary Therapies for Attention Deficit hyperactivity Disorder (ADHD)". Int. J Heal Caring, vol. 6, pp. 1-15. URL: http://www.wholist.ichealingresearch.com/user_files/ documents/ijhc/articles/EdMuse-6-2.pdf. May 31, 2006 (May 31, 2006) Abstract Only.

Sinn et al., "Effect of Supplementation with Polyunsaturated Fatty Acids and Micronutrients on Behavior and Learning Problems Associated with Child ADHD." J. of Bev. and Dev. Ped. 28:82-91 (2007).

* cited by examiner

*Primary Examiner* — Michael V Meller
(74) *Attorney, Agent, or Firm* — JMB Davis Ben-David

(57) ABSTRACT

Provided herein are compositions, methods of use thereof and kits comprising same for prophylaxis, alleviating or treating a subject with, or experiencing symptoms associated with, attention deficit disorder/attention deficit hyperactivity disorder (ADD/ADHD) and related disorders. Specifically, the compositions comprise a magnesium mineral, vitamin D and at least one botanical component, in amounts such that the supplement is effective for preventing, alleviating and/or treating a child, teen or adult subject with ADD/ADHD and related disorders or one or more symptoms associated with ADD/ADHD and related disorders.

14 Claims, No Drawings

DIETARY SUPPLEMENTS FOR TREATING ADHD AND RELATED DISORDERS

RELATED APPLICATIONS

This is a Continuation of co-pending U.S. patent application Ser. No. 15/023,390, filed Mar. 20, 2016, which is the U.S. National Stage of International Application No. PCT/IL2014/050828, filed Sep. 16, 2014, which, which in turn claimed the benefit of U.S. Provisional Application Ser. No. 61/880,185 filed Sep. 20, 2013 entitled "DIETARY SUPPLEMENTS FOR TREATING ADHD AND RELATED DISORDERS" and of U.S. Provisional Application Ser. No. 62/021,225 filed Jul. 7, 2014 entitled "DIETARY SUPPLEMENTS FOR TREATING ADHD AND RELATED DISORDERS." The foregoing patent applications are incorporated herein by reference in their entirety and for all purposes.

FIELD OF THE INVENTION

Provided herein are compositions and methods of use thereof useful for prophylaxis, alleviating or treating a subject with, or experiencing symptoms associated with, attention deficit disorder/attention deficit hyperactivity disorder (ADD/ADHD) and related disorders. The compositions are dietary supplements, intended for oral administration, that provide a solution for treating the above mentioned disorders and/or symptoms. Specifically, the compositions comprise a magnesium mineral, vitamin D and at least one botanical component, in amounts such that the supplement is effective for preventing, alleviating and/or treating a subject with ADD/ADHD and related disorders or one or more symptoms associated with ADD/ADHD and related disorders.

BACKGROUND OF THE INVENTION

Attention deficit disorder/attention deficit hyperactivity disorder (ADD/ADHD) and related disorders are common in children, adolescents and adults. The recent increase in the number of cases of attention deficit hyperactivity disorder (ADHD) and related disorders has been accompanied by a surge in the use of prescription psychopharmacological treatments. Stimulants such as methylphenidate (Ritalin) and amphetamines are the most common type of medication used for treating ADHD. These medications can activate brain circuits that support attention and focused behavior. Ritalin is a class 2 narcotic, with risk of abuse. Other non-stimulant medications, such as atomoxetine, guanfacine, and clonidine, are also available. For many children, ADHD medications reduce hyperactivity and impulsivity and improve their ability to focus, work, and learn. However, children taking medications must be monitored closely and carefully for compliancy, and for the commonly reported side-effects such as decreased appetite, sleep problems, anxiety and irritability. Some children report mild stomach aches or headaches. Other, less frequent side effects include cardiovascular or psychiatric problems.

Adults with ADHD are treated with medication, psychotherapy, or a combination of treatments. However, adult prescriptions for stimulants and other medications require special considerations, including the need to avoid dangerous drug interactions with commonly used medications for physical problems such as diabetes, high blood pressure, high cholesterol, anxiety and depression etc.

There remains a need for a safe and effective treatment for ADHD and related disorders.

SUMMARY OF THE INVENTION

Provided herein are compositions which include, natural ingredients and which are useful in treating a subject with ADD/ADHD or a related disorder or one or more symptoms of ADD/ADHD.

In one aspect provided herein is a tripartite composition comprising magnesium, vitamin D3 and a botanical component selected from *Valerian* spp and *Salvia* spp; and a pharmacologically acceptable carrier or excipient. In various embodiments, the magnesium is magnesium citrate, although other magnesium salts are acceptable. Preferably, magnesium is present in a dose amount of 50 mg to 500 mg (milligram elemental Mg) or 75 mg to 300 mg, preferably about 80 mg to about 160 mg elemental Mg. The magnesium may be in the form of magnesium carbonate, magnesium oxide, magnesium lactate, magnesium citrate etc. In some embodiments, vitamin D3 is present in a dose amount of 50 IU to 1000 IU (international units) or 100 to 500 IU, preferably about 200 to 400 IU or 400 IU.

One preferred botanical component or ingredient, is a root extract from a *Valerian* species, preferably *Valerian officinalis* or *Valerian edulis*. In some embodiments the *Valerian* spp root extract is a root extract from *Valerian officinalis*, present in a dose amount of 20 mg to 500 mg or 50 to 300 mg, preferably about 100 mg to 200 mg. In some embodiments the *Valerian* spp root extract is a dry root extract from *Valerian edulis* present in a dose amount of 20 mg to 500 mg or 50 mg to 300 mg, preferably about 100 mg to 200 mg. In some embodiments, a lipophilic extract of *Valerian* species extract is preferred.

A second preferred botanical component or ingredient is an oil or dry extract from a *Salvia* species, preferably *Salvia sclarea* oil extract, present in a dose amount of 10 microL to 250 microL, or 50 microL to 100 microL, preferably about 50 microL (microliter) or *Salvia sclarea* dry leaf extract (e.g. finely ground dry leaves) in a dose amount of 50 mg to 1000 mg, or about 150 mg to about 750 mg; or about 250 mg to 500 mg.

The compositions disclosed herein are essentially caffeine free and theanine free.

Additional components or ingredients may be included in the composition to enhance its effect in treating ADHD or to alleviate the symptoms of ADHD.

Accordingly, the composition may further include one or more of iron, calcium, an omega 3 fatty acid, mixture of omega 3 fatty acids, an omega 9 fatty acid, vitamin E, vitamin B6 and gingko *biloba*.

In some embodiments, the composition includes iron as iron fumarate, although other iron salts are acceptable. In some embodiments, the composition includes iron in a dose amount of 10 mcg to 160 mcg or 20 mcg to 80 mcg, preferably about 20 mcg to 60 mcg (microgram elemental Fe). In some embodiments, the composition includes iron as iron salt for example, iron bisglycinate or iron fumarate.

In some embodiments, the composition includes calcium as calcium carbonate, although other calcium salts are acceptable. In some embodiments, the composition includes calcium in a dose amount of 50 mg to 500 mg or 75 to 300 mg, preferably about 100 mg to 150 mg and up to 200 mg (milligram elemental Ca).

In some embodiments, the composition includes an omega 3 fatty acid or a mixture of omega 3 fatty acids. The preferred omega 3 fatty acids are ALA (alpha-linolenic acid), EPA (eicosapentaenoic acid) and DHA (docosahexaenoic acid) although other natural and non-natural omega 3 fatty acids are acceptable. In some embodiments, the omega 3 fatty acids are from animal and plant origin. In some embodiments, the omega 3 fatty acids are synthetic. In some embodiments, the composition includes omega 3 fatty acid at a dose of about 100-1100 mg. In some embodiments the omega 3 fatty acids include a mixture of EPA and DHA, each in an amount of 100 mg to 1100 mg or 250 mg to 700 mg, preferably about 300 mg to about 550 mg. In some embodiments, EPA is present in an amount of about 500 mg to about 600 mg per dose. In some embodiments, DHA is present in an amount of about 300 mg to about 400 mg per dose. In some embodiments the composition further includes omega 9 fatty acid in an amount of about 10 mg to about 1,000 mg per dose, preferably about 300 mg.

In some embodiments, the composition includes vitamin B6. A preferred Vitamin B6 is pyroxidine (hydrochloride form of Vitamin B6). In some embodiments, the composition includes pyridoxine at a dose amount of 0.1 mg to 20 mg, or 1 mg to 5 mg, preferably about 1.0 mg to about 2.0 mg.

In some embodiments the composition includes an extract of gingko *biloba*, wherein the gingko *biloba* is present as a leaf extract at a dose amount of 10 mg to 200 mg, or 50 mg to 100 mg, preferably about 80 mg. In some embodiments, the composition comprises gingko *biloba* extract and *Salvia sclarea* oil extract or *Salvia sclarea* dry leaf extract.

A dose or dose amount refers to the amount (e.g. microgram, milligram, milliliter) of each ingredient per day. The composition may be provided in one or more formulations such that the magnesium, vitamin D3 and botanical component are present together in a single formulation or in separate formulations in a single kit. A single formulation may provide the three ingredients in, for example, a tablet, softgel or capsule (e.g. a "unit"). Alternatively the three ingredients may be provided in two separate formulations wherein, for example, the lipid(s) (i.e. vitamin D etc.) is separate from the non-lipid ingredients (i.e. magnesium and other minerals, botanical etc.).

In one embodiment, a preferred composition comprises magnesium citrate in a dose amount of 80 mg to 160 mg (milligram elemental Mg), vitamin D3 in a dose amount of about 200-400 IU, preferably about 400 IU, and *Valerian* spp root extract in a dose amount of about 100 mg. In various embodiments, the composition may further include one or more of iron, calcium, an omega 3 fatty acid/mixture of omega 3 fatty acids, vitamin B6 and gingko *biloba*. In various embodiments, the composition further includes iron, calcium, an omega 3 fatty acid mixture and vitamin B6, further optionally Vitamin E and/or C or a derivative thereof.

A preferred composition consists essentially of magnesium as magnesium citrate in a dose amount of about 80 mg to 160 mg (milligram elemental Mg), vitamin D3 in a dose amount of about 200-400 IU, *Valerian* spp root extract in a dose amount of about 100 mg, iron as iron fumarate in a dose amount of about 20 to 40 mcg (microgram elemental Fe), calcium as calcium carbonate in a dose amount of about 100 mg to 200 mg (milligram elemental Ca), an omega 3 fatty acid or mixture of omega 3 fatty acids in a dose amount of about 500 mg-1100 mg, and vitamin B6 (pyridoxine hydrochloride) in a dose amount of about 1.0 mg to 2.0 mg.

In some embodiments, a preferred composition is a single formulation composition, which consists essentially of magnesium as magnesium citrate in a dose amount of about 80 mg to 240 mg (milligram elemental Mg), vitamin D3 in a dose amount of about 200-400 IU, *Valerian* spp root extract in a dose amount of about 100 to 300 mg, iron as iron fumarate in a dose amount of about 20 to 60 mcg (microgram elemental Fe), calcium as calcium carbonate in a dose amount of about 100 mg to 300 mg (milligram elemental Ca), an omega 3 fatty acid or mixture of omega 3 fatty acids in a dose amount of about 500 mg-1100 mg, and vitamin B6 (pyridoxine hydrochloride) in a dose amount of about 1.0 mg to 3.0 mg.

In another embodiment, a preferred composition is a single formulation composition, which consists essentially of magnesium as magnesium citrate in a dose amount of about 80 mg to 160 mg (milligram elemental Mg), vitamin D3 in a dose amount of about 200-400 IU, *Valerian* spp root extract in a dose amount of about 100 mg to 200 mg, iron as iron fumarate in a dose amount of about 20 mcg to 40 mcg (microgram elemental Fe), calcium as calcium carbonate in a dose amount of about 100 mg to 200 mg (milligram elemental Ca), and vitamin B6 (pyridoxine hydrochloride) in a dose amount of about 1.0 mg to 2.0 mg.

In another embodiment, the composition comprises is a two formulation composition, one a liquid formulation comprising the Vitamin D3 and the second formulation a solid or semi-solid formulation comprising the botanical ingredient (e.g. *Valerian* or *Ginkgo biloba*) and the magnesium. The liquid formulation comprises from 50 IU to 1000 IU (international units) or 100 to 500 IU per dose, preferably about 200 to 400 IU per dose or 400 IU vitamin D3 per dose. In some embodiments, the liquid formulation may include the botanical component, for example *Salvia* spp. oil extract.

The liquid formulation may further include other lipid, or fat soluble ingredients, for example Vitamin E, one or more fatty acid and/or vegetable oils. In various embodiments the liquid formulation includes 400 IU Vitamin D3 and 0.75 mg Vitamin E per dose. The liquid formulation preferably includes 900-1100 mg omega 3 fatty acids including a mixture of DHA and EPA, and about 300 mg omega 9 fatty acids. A dose amount of the liquid formulation may be from about 100 mcl (microliter) to about 10 ml or about 500 mcl to about 5 ml. A preferred dose amount is 3 ml and includes 400 IU Vitamin D3 and one or more of fatty acids, fat soluble vitamin and antioxidants or preservatives.

Each solid or semi-solid unit includes about 50-100 mg *Valerian* spp extract and about 40-80 mg elemental magnesium (e.g. as magnesium citrate). Additional ingredients may include calcium as calcium carbonate (about 50-100 mg elemental Ca); iron as iron bisglycinate (about 10-50 mcg elemental Fe), Vitamin B6 (about 0.1-10 mg), and one or more additional botanical element. In some embodiments, the solid or semi-solid unit includes *Ginkgo biloba* or *Salvia sclarea*, or preferably *Ginkgo biloba* and *Salvia sclarea*, instead of *Valerian* spp. A dose or dose amount includes for example one, 2, 3 or 4 units.

In another embodiment, a preferred composition comprises magnesium in a dose amount of 80 mg to 100 mg (milligram elemental Mg as e.g. magnesium citrate), vitamin D3 in a dose amount of about 400 IU, and *Salvia sclarea* oil extract in a dose amount of about 50 microL or dry leaf extract in a dose amount 50 mg to 1000 mg, preferably about 250 mg to 500 mg. In various embodiments, the composition may further include one or more of iron, calcium, an omega 3 fatty acid/mixture of omega 3 fatty acids, an omega 9 fatty acid, vitamin B6, vitamin E and gingko *biloba*. In preferred embodiments, the composition further includes iron, calcium, an omega 3 fatty acid/mixture of omega 3 fatty acids, an omega 9 fatty acid vitamin B6, vitamin E and *Ginkgo biloba*.

A preferred composition consists essentially of magnesium in a dose amount of about 80 mg to 160 mg (milligram elemental Mg as e.g. magnesium citrate), vitamin D3 in a dose amount of about 400 IU, *Salvia sclarea* oil extract in a dose amount of about 50 microL or *Salvia* dry leaf extract in a dose amount of about 250 mg; iron fumarate or iron bisglycinate in a dose amount of about 20-60 mcg (microgram elemental iron), calcium in a dose amount of about 100 mg (milligram elemental Ca, as, e.g. calcium carbonate), an omega 3 fatty acid/mixture of omega 3 fatty acids in a dose amount of about 500-1100 mg, vitamin B6 (pyridoxine hydrochloride) in a dose amount of about 1.5 mg, and gingko *biloba* as a leaf extract at a dose amount of about 80 mg.

In preferred embodiments, the composition is formulated for oral administration as a liquid gel capsule, a soft gel capsule, a tablet, a chewable tablet, a chewable wafer, an extended release formulation, a "gummy" candy (chewable lozenge; e.g. pectin or gelatin base), a lozenge, a pastille (e.g. polyol base), chewing gum, an effervescing tablet, or a liquid formulation. Each recommended amount of such liquid gel capsule, a soft gel capsule, a tablet, a chewable tablet, a chewable wafer, an extended release formulation, a "gummy" candy, lozenge, pastille, chewing gum, an effervescing tablet, may be considered a "dose". In some embodiments, the composition further comprises one or more of a natural flavoring agent, artificial flavoring agent, natural colorant, artificial colorant and sweetening agent. The composition may include varied and numerous inactive ingredients known within the art to improve the formulation, delivery, preservation, appearance, palatability and administration of the active ingredients.

In some embodiments, the composition is formulated for oral administration as a chewable tablet, or as a "gummy" candy. In preferred embodiments, the composition comprising magnesium citrate in a dose amount of 80 mg to 100 mg, vitamin D3 in a dose amount of about 200-400 IU, and *Valerian* spp root extract in a dose amount of about 100 mg is formulated for oral administration as a chewable tablet, or as a "gummy" candy.

In some embodiments, the composition is formulated for oral administration as a liquid gel capsule, soft gel capsule or as a tablet. In preferred embodiments, the composition comprising magnesium citrate in a dose amount of 80 mg to 100 mg, vitamin D3 in a dose amount of about 200-400 IU, and *Salvia sclarea* oil extract in a dose amount of about 50 microL or microL or *Salvia sclarea* dry leaf extract (e.g. finely ground dry leaves) in a dose amount of about 250 mg to about 500 mg is formulated for oral administration as a soft gel capsule.

In another embodiment, a preferred composition comprises magnesium (as magnesium citrate) in a dose amount of 80 mg to 160 mg, vitamin D3 in a dose amount of about 200-400 IU, and *Salvia sclarea* oil extract in a dose amount of about 50 microL. In various embodiments, the composition may further include one or more of iron, calcium, an omega 3 fatty acid/mixture of omega 3 fatty acids, an omega 9 fatty acid, vitamin B6, vitamin E and *Ginkgo biloba*. In preferred embodiments, the composition further includes iron, calcium, vitamin B6 and *Ginkgo biloba* and is formulated as a soft gel, utilizing a soft gel shell comprising at least one omega 3 fatty acid.

A preferred composition consists essentially of magnesium (as magnesium citrate) in a dose amount of about 100 mg, vitamin D3 in a dose amount of about 400 IU, *Salvia sclarea* oil extract in a dose amount of about 50 microL or *Salvia sclarea* dry leaf extract in a dose amount of about 250 mg to 500 mg; iron (as iron fumarate or iron bisglycinte) in a dose amount of about 20-60 mcg, calcium (as calcium carbonate) in a dose amount of about 100 mg, vitamin B6 (pyridoxine hydrochloride) in a dose amount of about 1.0 mg to 2.0 mg, and gingko *biloba* as a leaf extract at a dose amount of about 80 mg and is formulated as a soft gel, utilizing a soft gel shell comprising at least one omega 3 fatty acid wherein the omega 3 is present at a dose amount of about 100 mg to about 1100 mg.

In a second aspect, provided herein is a method for treating ADD/ADHD or related disorders in a subject in need thereof, the method comprising administering to the subject a composition comprising magnesium, vitamin D3 and a botanical component selected from the group consisting of *Valerian* spp and *Salvia sclarea*, in a dose effective for treating ADD/ADHD or related disorders in the subject. Preferably, the method of treating ADD/ADHD includes alleviating one or more of the symptoms selected from the group consisting of reduced concentration or focus, hyperactivity, forgetfulness and impulsivity.

In a third aspect, provided is use of a composition comprising magnesium, vitamin D3 and a botanical component selected from the group consisting of *Valerian* spp and *Salvia sclarea*, in a dose effective for treating ADD/ADHD or related disorders.

In another aspect, provided is a kit comprising magnesium, vitamin D3 and a botanical component selected from the group consisting of *Valerian* spp and *Salvia sclarea*, in amounts effective for treating ADD/ADHD or related disorders in the subject. In preferred embodiments of the kit, the kit composition comprises two formulations, a liquid formulation and a solid of semi-solid formulation.

According to the composition, method, use or kit, a botanical component or ingredient, is a root extract from a *Valerian* species, preferably *Valerian officinalis* or *Valerian edulis*. In some embodiments of the composition, method, use or kit the *Valerian* spp root extract is a root extract from *Valerian officinalis*, present in a dose amount of 20 mg to 500 mg or 50 to 300 mg, preferably about 100 mg to 150 mg. In some embodiments the *Valerian* spp root extract is a dry root extract from *Valerian edulis* present in a dose amount of 20 mg to 500 mg or 50 to 300 mg, preferably about 100 mg to 150 mg.

An alternate botanical component or ingredient is a *Salvia sclarea* oil extract, present in a dose amount of 10 microL to 250 microL or 50 microL to 100 microL, preferably about 50 microL (microliter) or *Salvia sclarea* dry leaf extract in a dose amount of about 250 mg to 500 mg. Additional components or ingredients may be included in the composition to enhance its effect in treating ADHD or to alleviate the symptoms of ADHD.

In certain embodiments of the composition, method, use or kit, the composition may further include one or more of iron, calcium, an omega 3 fatty acid/mixture of omega 3 fatty acids, an omega 9 fatty acid, vitamin E, vitamin B6 and gingko *biloba*, and optionally one or more antioxidant.

In some embodiments of the composition, method, use or kit, the composition includes iron as iron fumarate, although other iron salts such as iron bisglycinate are acceptable. In some embodiments, the composition includes iron (as iron fumarate or iron bisglycinate) in a dose amount of 10 mcg to 100 mcg or 20 mcg to 40 mcg, preferably about 20 mcg to 60 mcg (microgram elemental Fe) or about 10 mcg to 30 mcg for a child or adult. In some embodiments, the composition includes calcium as calcium carbonate, although other calcium salts are acceptable. In some embodiments, the composition includes calcium carbonate in a dose amount of 50 mg to 500 mg or 75 mg to 300 mg, preferably about 100 mg to 150 mg (milligram elemental Ca).

In various embodiment of the composition, method, use or kit, the composition includes an omega 3 fatty acid or a mixture of two or more omega 3 fatty acids. The preferred omega 3 fatty acids are EPA (eicosapentaenoic acid) and DHA (docosahexaenoic acid) although other natural and non-natural omega 3 fatty acids are acceptable. In some embodiments, the composition includes omega 3 fatty acid or a mixture of omega 3 fatty acids at a dose of 100 mg to 1100 mg or 250 mg to 700 mg, preferably about 900 mg to 1000 mg. In some embodiments, the composition includes vitamin B6. A preferred Vitamin B6 is pyroxidine (hydrochloride form of Vitamin B6). In some embodiments, the composition includes vitamin B6 (pyridoxine hydrochloride) at a dose amount of 0.1 mg to 20 mg or 1 mg to 5 mg, preferably about 1.5 mg to 3 mg. In some embodiments the composition includes an extract of gingko *biloba*, wherein the gingko *biloba* is present as a leaf extract at a dose amount of 10 mg to 200 mg, or 50 mg to 100 mg, preferably about 80 mg. In some embodiments, the gingko *biloba* extract is present in a composition with *Salvia sclarea* oil extract or *Salvia sclarea* dry leaf extract.

In one embodiment of the composition, method, use or kit, a preferred composition comprises magnesium citrate in a dose amount of 80 mg to 160 mg (milligram elemental Mg), vitamin D3 in a dose amount of about 200-400 IU, and *Valerian* spp root extract in a dose amount of about 100 mg to 150 mg. In various embodiments, the composition may further include one or more of iron, calcium, an omega 3 fatty acid, an omega 9 fatty acid, vitamin B6, vitamin E and gingko *biloba*. In various embodiments, the composition further includes iron, calcium, an omega 3 fatty acid and vitamin B6. A preferred composition consists essentially of magnesium (as magnesium citrate) in a dose amount of about 80 mg to 160 mg (milligram elemental Mg), vitamin D3 in a dose amount of about 200-400 IU, *Valerian* spp root extract in a dose amount of about 100 mg, iron (as iron fumarate) in a dose amount of about 20 mg to 40 mcg (microgram elemental Fe), calcium (as calcium carbonate) in a dose amount of about 100 mg to 200 mg (milligram elemental a), an omega 3 fatty acid/mixture of omega 3 fatty acids in a dose amount of about 500-1100 mg, and pyridoxine in a dose amount of about 1.0 mg to 2.0 mg. A kit may include, for example, 10 to 1000 capsules, softgel or tablets, or about 30 to 90 capsules, softgel or tablets, each capsule, softgel or tablet having about 50 mg *Valerian* spp root extract, about 40 mg magnesium provided as magnesium citrate, and about 200-400 IU Vitamin D3 and may further include for example one or more about 50 mg calcium provided as calcium carbonate, about 10 microgram iron provided as iron bisglycinate and about 0.5 mg Vitamin B6, and omega 3 fatty acids. A package insert may provide instructions to ingest 2-3 tablets, softgels or capsules per day (dose amount).

A kit may include a two formulation composition comprising a solid or semi-solid formulation (e.g. tablets, softgels, and capsules) and a liquid formulation. For example, 10 to 1000 capsules, softgels or tablets, or about 30 to 90 capsules, softgel or tablets, each capsule, softgel or tablet having about 50 mg *Valerian* spp root extract, about 40 mg magnesium provided as magnesium citrate, and may further include for example about 50 mg calcium provided as calcium carbonate, about 10 microgram iron provided as iron bisglycinate and about 0.5 mg Vitamin B6. The kit further includes a liquid formulation comprising 30 to 150 ml wherein each dose (.about.1-5 ml) includes about 1200 mg mixture of omega 3 with omega 9 fatty acids and 400 IU vitamin D3. A package insert may provide instructions to ingest 2-3 tablets or capsules per day (dose amount) and an amount, for example, of 1-5 ml of the liquid formulation.

In another embodiment of the composition, method, use or kit a preferred composition comprises magnesium (as magnesium citrate) in a dose amount of 80 mg to 100 mg (milligram elemental Mg), vitamin D3 in a dose amount of about 200-400 IU, and *Salvia sclarea* oil extract in a dose amount of about 50 microL. In various embodiments, the composition may further include one or more of iron, calcium, an omega 3 fatty acid, an omega 9 fatty acid, vitamin B6, vitamin E and gingko *biloba*. In preferred embodiments, the composition further includes iron, calcium, an omega 3 fatty acid, vitamin B6 and gingko *biloba*. A preferred composition consists essentially of magnesium (as magnesium citrate) in a dose amount of about 100 mg (milligram elemental Mg), vitamin D3 in a dose amount of about 200-400 IU, *Salvia sclarea* oil extract in a dose amount of about 50 microL or *Salvia sclarea* dry leaf extract in a dose amount of 250 mg to 500 mg; iron (as iron fumarate) in a dose amount of about 20-50 mcg (milligram elemental Fe), calcium (as calcium carbonate) in a dose amount of about 100 mg (milligram elemental Ca), an omega 3 fatty acid//mixture of omega 3 fatty acids in a dose amount of about 500-1100 mg, vitamin B6 (pyridoxine hydrochloride) in a dose amount of about 1.5 mg, and gingko *biloba* as a leaf extract at a dose amount of about 80 mg.

In certain embodiments of the composition, method, use or kit the composition is formulated for oral administration as a liquid capsule, a soft gel capsule, a tablet, a chewable tablet, a chewable wafer, an extended release formulation, a "gummy" candy, a lozenge, a pastille, chewing gum, an effervescing tablet, and/or a liquid formulation. In some embodiments, the composition further comprises one or more of a natural flavoring agent, artificial flavoring agent, natural colorant, artificial colorant and sweetening agent.

In various embodiments of the composition, method, use or kit the composition is a two formulation composition, whereby one formulation is a liquid formulation and the second formulation is a solid or semi-solid formulation. According to the method, use or kit the liquid formulation and solid or semi-solid formulation are taken at about the same time, for example within a few seconds, a few minutes or a few hours of each other.

In some embodiments of the composition, method, use or kit, the liquid formulation includes Vitamin D3 and may include for example one or more of omega 3 fatty acid, omega 9 fatty acid, and Vitamin E. A dose of about 0.1 to about 5 ml includes for example about 400 IU Vitamin D3 and 0.75 mg Vitamin E. The liquid formulation may further include for example soy lecithin and/or ascorbyl palmitate (a vitamin C ester, for example as a preservative). The liquid formulation preferably includes 500 mg to 1100-mg omega 3 fatty acids including DHA and EPA, and about 300 mg omega 9 fatty acids. A dose amount of the liquid formulation may be from about 100 mcl (microliter) to about 10 ml or about 500 mcl to about 5 ml. A preferred dose amount is 3 ml and includes 400 IU Vitamin D3 and one or more of fatty acids, fat soluble vitamin and antioxidants or preservatives.

The solid or semi-solid formulation includes the *Valerian* spp extract and the magnesium and may include for example, a calcium salt, an iron salt and/or vitamins such as Vitamin B6. Each capsule or tablet includes for example about 50 mg-100 mg *Valerian* spp extract, 50-mg-100 mg elemental calcium (e.g. as calcium carbonate), 40 mg-80 mg elemental magnesium (e.g. as magnesium citrate), 10-20 mcg iron elemental (e.g. as iron bisglycinate) and 0.1-2 mg Vitamin B6. The solid or semi-solid formulation may further include fatty acids and or additional vitamins. In some embodiments, a solid dose form is preferred (e.g. tablet, solid capsule); in some embodiments, a semi-solid dose form is preferred (e.g. softgel, liquid capsule)

In some embodiments, the dose amount for a child aged about 6 to 10 years old is one solid or semi-solid unit (e.g. table, softgel, capsule, gummy etc.) and a liquid dose (3 ml) once a day, while the dose amount for a preteen or teenager about 11 to 14 years old is s 2 solid or semi-solid units and one liquid dose (3 ml) once a day. Alternatively, a teenager or adult (aged 15 and older) may be administered (including self administration) one liquid dose (3 ml) once a day and 1 solid or semi-solid dose form twice or thrice a day. In some embodiments, the subject will not ingest more than 400 IU of Vitamin D3 per day (24 hours) from the liquid formulation.

In some embodiments of the composition, method, use or kit the composition is formulated and administered orally as a chewable tablet, or as a "gummy" candy. In preferred embodiments, the composition comprising magnesium in a dose amount of 80 mg to 100 mg (milligram elemental Mg), vitamin D3 in a dose amount of about 200-400 IU, and *Valerian* spp. root extract in a dose amount of about 100 mg is formulated for oral administration as a chewable tablet, or as a "gummy" candy. The gummy candy may further include any one of the components described above, for example calcium, iron, omega 3/mixture of omega 3 etc.

In other embodiments of the composition, method, use or kit, the composition is formulated and administered orally as a liquid gel capsule, soft gel capsule or as a tablet. In preferred embodiments, the composition comprising magnesium citrate in a dose amount of 80 mg to 100 mg (milligram elemental Mg), vitamin D3 in a dose amount of about 200-400 IU, and *Salvia sclarea* oil extract in a dose amount of about 50 microL or *Salvia sclarea* dry leaf extract in a dose amount of 250 mg to 500 mg is formulated for oral administration as a soft gel capsule. Preferably, the composition comprising the *Salvia* (e.g. *Salvia sclarea*) further comprises *Ginkgo biloba* (for example as a leaf extract) at a dose amount of about 80 mg.

In certain embodiments of the composition, method, use or kit, the composition is administered to the subject daily. In preferred embodiments of the composition, method, use or kit, the composition is administered to the subject, twice, thrice or four times a day. In preferred embodiments, the liquid and solid or semi-solid formulations are administered (including self administration) once daily.

In another aspect, provided herein is a composition for use in treating ADHD or a related disorder, the composition comprising magnesium, vitamin D3 and a botanical component selected from the group consisting of *Valerian* spp and *Salvia sclarea*; and a pharmacologically acceptable carrier or excipient.

This disclosure is intended to cover any and all adaptations or variations of combination of features that are disclosed in the various embodiments herein. Although specific embodiments have been illustrated and described herein, it should be appreciated that the invention encompasses any arrangement of the features of these embodiments to achieve the same purpose. Combinations of the above features, to form embodiments not specifically described herein, will be apparent to those of skill in the art upon reviewing the instant description.

DETAILED DESCRIPTION OF THE INVENTION

Disclosed herein are safe and all natural compositions useful in the treatment of ADHD and related disorders and/or the symptoms of ADHD and related disorders.

Advantageously, the dietary supplements disclosed herein provide an over the counter and side effect-free treatment option for children, adolescents and adults afflicted with ADHD and related disorders. Medications currently on the market are known to cause adverse side effects and pose a risk for dangerous drug interactions in certain individuals.

The compositions are dietary supplements which include a combination of active ingredients that act synergistically to provide a natural and healthy option to prescription drugs. The active ingredients play critical roles in cellular metabolism. Without wishing to be bound to theory, the compositions protect the energy balance in cells of the nervous system, to achieve optimal brain function and improve cognitive function including memory, concentration and focus.

The compositions provided herein include natural ingredients in dose amounts compatible with a healthy body and mind. The compositions are naturally low in sugar and do not cause a spike in blood sugar. The compositions are also low in fat soluble vitamins and other potentially vitamins or minerals that may be harmful or toxic at high doses.

The compositions include as the three primary components, magnesium, vitamin D3 and a botanical selected from *Valerian* spp. and *Salvia* spp.

Magnesium is an essential mineral for human health as it is required in all cell types and is involved in hundreds of biochemical reactions in the body. One of magnesium's properties is aiding the absorption of calcium in the body and to maintaining the energy generating mitochondria in all cells. Magnesium is believed to assist in preventing osteoporosis, insomnia, constipation, heart attacks, hypertension, constipation, kidney stones, gallstones and migraines. Good dietary sources of magnesium include almonds, whole grains, wheat germ and green leafy vegetables. Often, magnesium requirements cannot be met from diet alone. There have been some reports of a link between magnesium deficiency and ADHD, see for example the abstract from Starobrat-Hermelin and Kozielic, Magnes Res. (1997) 10(2):149-156. Some side effects of high dose magnesium supplements (e.g. greater than about 600 mg) include stomach upset, nausea, vomiting and diarrhea.

A person with skill in the art will be able to easily calculate preferred dose amounts of mineral compounds (e.g. mineral salts) based on the amount of elemental mineral provided. Magnesium supplements come in different salt forms, e.g. citrate, oxide, carbonate and the like. A preferred salt of magnesium is magnesium citrate, which may exhibit better uptake, better bioavailability and fewer side effects than other magnesium salts. Magnesium is preferably present in the dose amount of about 40-500 mg elemental magnesium (Mg).

Another option is, for example, magnesium L-threonate such as in the product, Magtein™ commercially available for enhancing cognitive function, mood and sleep.

Vitamin D3, also known as cholecalciferol, belongs to a group of fat soluble vitamins. Vitamin D3 can be synthesized by the body, specifically the skin upon exposure to sunlight. A diet deficient in vitamin D together with inadequate sun exposure can cause bone softening and increased risk for bone fractures (osteomalacia in adults and rickets when it occurs in children). As vitamin D3 is a fat soluble vitamin, toxicity can occur by overdosing dietary supplements. Dose amount for Vitamin D3 are given in International Units (IU), whereby 40 IU are equal to 1 microgram (mcg). The Institute of Medicine (TOM) Recommended Dietary Allowance of vitamin D is 400 IU per day for children younger than 1 year of age, 600 IU per day for children at least 1 year of age and adults up to 70 years, and 800 IU per day for older adults. The US Institute of Medicine concluded that serum 25-hydroxyvitamin D [25(OH)D] of 20 ng/ml or more will cover the requirements of 97.5% of the population. The US Endocrine Society's Clinical Practice Guideline suggested that 400-1000 IU per day may be needed for children aged less than 1 year, 600-1000 IU per day for children aged 1 year or more, and 1500-2000 IU per day for adults aged 19 years or more to maintain 25(OH)D above the optimal level of 30 ng/ml.

The term "botanical component" refers to any component of a plant including, for example, the leaves, flowers, fruit, stems, roots, seeds, exudates and combinations thereof. The compositions disclosed herein include as a primary ingredient either *Valerian* spp., preferably *Valerian officinalis* or *Valerian edulis* root extract, or a *Salvia* spp extract, preferably *Salvia sclarea* oil extract and may further include one or more extracts. An "extract" is any compound, any agent, or mixtures thereof (including but not limited to an extract of plant material) that are derived from plant material. Extract includes for example, dry material (e.g. roots, leaves, petals), aqueous or lipophilic extracts.

*Valerian officinalis* has been used as a medicinal herb for centuries. *Valerian* root extract product has historically been administered as a sleeping aid and to reduce anxiety. Without wishing to be bound to theory, *Valerian* root extract product causes the release of gamma-aminobutyric acid (GABA) and inhibits the action of GABA transaminase, the enzyme that destroys the neurotransmitter. The composition disclosed herein includes *Valerian* root extract, preferably *Valerian officinalis* root extract, at a dose amount of 20 mg to about 500 mg, 50 mg to 300 mg, preferably about 100 mg.

Common types of sage herb are clary sage (*Salvia sclarea*), Spanish sage (*Salvia* lavandulaefolia) and glutinous sage (*Salvia glutinosa*). *Salvia sclarea* is reported to have a range of therapeutic effects including anti-microbial (bacterial, fungal and viral), blood sugar lowering activity and antioxidants which have liver protective properties. *Salvia sclarea* has been shown to possess in vitro cholinesterase inhibiting properties, and to thereby improve mood. *Salvia* can be used in any form, for example, oil extract or powdered dried leaves or root. In some embodiments, a composition disclosed herein includes *Salvia sclarea* and *Ginkgo biloba*. Such composition is useful for treatment of adults (about 20 years and older) who have some of the symptoms of ADD (forgetfulness, lack of focus, etc.) in absence of hyperactivity.

The compositions disclosed herein, may further include iron, a mineral primarily found in the hemoglobin of red blood cells and in the myoglobin of muscle cells. Iron is required by the body for transporting oxygen and carbon dioxide. Iron supplements are typically taken by children, pregnant women and premenopausal women for preventing and treating iron deficiency and anemia. Several forms of iron salts are acceptable in the compositions disclosed herein, however, iron fumarate or iron bisglycinate are preferred. Iron is preferably present in the composition at a dose amount of about 20-60 mcg elemental iron (Fe).

The compositions disclosed herein, may further include calcium, a mineral that is an essential component of bones and teeth and plays roles in a variety of biochemical pathways. A calcium salt in the compositions disclosed herein is for example, calcium acetate, calcium citrate, calcium lactate or calcium carbonate. Calcium is preferably present in the composition at a dose amount of about 100-300 mg elemental calcium (Ca) as calcium carbonate.

The compositions disclosed herein, may further include vitamins B6, important in maintaining metabolism, generating energy and the functioning of the nervous system. The preferred form of Vitamin B6 is pyroxidine. The composition disclosed herein includes a dose amount of 0.1 mg to 20 mg, or 1 mg to 5 mg, preferably about 1.0 mg to 2.0 pyroxidine. For example a dose of more than 5 mg Vitamin B6 per day may be valuable to a subject who engages heavily in sport.

The compositions disclosed herein optionally include omega-3 fatty acids. Omega-3 fatty acids are polyunsaturated fatty acids that cannot be synthesized by the body, hence are "essential" fatty acids that must be taken in by food or supplements. Omega-3 fatty acids are crucial in the development and function of neurons and a supplement can help improve cognitive functions including memory, focus and concentration and assist in alleviating anxiety. Preferred omega-3 fatty acids are alpha-linolenic acid (ALA), eicosapentaenoic acid (EPA) and docosahexaenoic acid (DHA), however, other omega 3 fatty acids are acceptable in the compositions disclosed herein. Non-limiting examples include stearidonic acid, eicosatrienoic acid, eicosatetraenoic acid, docosapentaenoic acid, tetracosapentaenoic acid and tetracosahexaenoic acid. Omega-3 fatty acids are derived from animal or plant material, for example certain fish, flaxseed, nuts and seeds or are synthetic. In some embodiments, the composition includes omega 3 fatty acid at a dose of 100 mg to 1000 mg. In some embodiments, the omega 3 fatty acids include a mixture of EPA and DHA, each in amounts of 100 mg to 1100 mg or 250 mg to 700 mg, preferably about 300 mg to about 500 mg. In some embodiments, the omega 3 is a component of a soft gel shell. In various embodiments, the composition further includes omega 9 fatty acid. In various embodiments, the composition includes about 10 mg to about 500, or about 300 mg omega 9 fatty acid per dose.

The dietary supplements may further include gingko biloba (*Salisbura adiantifolia*) extract product. Gingko biloba extract is preferably leaf extract, which is believed to improve cognitive performance, specifically enhance memory.

The composition provided herein may further include ingredients to improve delivery, formulation and/or palatability. For example, the compositions disclosed herein, may also include any one or more of glidants, lubricants, binders, sweeteners, flavoring and coloring components. Any conventional sweetener or flavoring component may be used. Combinations of sweeteners, flavoring components, or sweeteners and flavoring components (synthetic and/or natural) may likewise be used.

Non-limiting examples of binders include acacia, tragacanth, gelatin, starch, cellulose based materials such as methyl cellulose and sodium carboxy methyl cellulose, alginic acids and salts thereof, magnesium, aluminum silicate, polyethylene glycol, guar gum, polysaccharide acids, bentonites, sugars, invert sugars and the like. Binders may be used in an amount of up to 60 weight percent and preferably about 10 to about 40 weight percent of the total composition.

Coloring agents are optional and may include known FD&C dyes and natural coloring agents such as grape skin extract, beet red powder, beta-carotene, annatto, carmine, turmeric, paprika, etc. The amount of coloring used may range from about 0.01 percent to about 3.5 weight percent of the total composition.

Flavoring agents are optional and may be incorporated in the composition may be chosen from synthetic flavors oils and flavoring aromatics, natural oils, plant extracts. Examples include cinnamon oil, oil of wintergreen, peppermint oil, clove oil, bay oil, anise oil, *eucalyptus*, thyme oil, cedar leaf oil, nutmeg oil, sage oil or almond oil. Examples of flavoring agents include, but are not limited to, almond, apple, banana, berry, bubblegum, caramel, citrus, cherry, chocolate, coconut, grape, green tea, honey, lemon, licorice, lime, mango, maple, mint, orange, peach, pineapple, raisin, strawberry, vanilla, watermelon and combinations thereof. Flavors may be present in an amount ranging from about 0.05 to about 3 percent by weight based upon the weight of the composition.

The composition provided herein may further include colorants, for example, to produce a composition more appealing to a child and encourage compliancy. Compositions may include natural and/or artificial colorants. The composition (liquid, solid and/or semi-solid) may further include one or more preservatives including antioxidants, for example Vitamin E or derivatives, flavonoid polyphenols (like EGCG from green tea and quercetin from apples); non-flavonoid polyphenols (like curcumin from turmeric and resveratrol from grapes); phenolic acids or phenolic diterpenes (like rosmarinic acid or carnosic acid from rosemary); or organosulfur compounds (like isothiocyanate, L-sulforaphane, from broccoli).

Gummies, lozenges, tablets etc. may be generated with sugar or as sugar free formulations. Preferably, the formulations are low in sugar (<40% sugar, preferably less than 30% or 20% sugar), or are sugar-free whereby a sugar substitute such as sorbitol, xylitol, mannitol, maltitol, and hydrogenated glucose or maltose syrups or maltodextrins in conjunction with acesulfame-K and/or aspartame may replace the sugar, in full or in part.

The compositions provided herein are essentially caffeine free and theanine-free. The effects of caffeine and theanine in children and adolescents, especially children and adolescents with ADD/ADHD, are potentially detrimental. Theanine and caffeine can also pose a risk for harmful drug interactions. "Essentially theanine-free" and "essentially caffeine free" as used herein means that the compositions contain less than about 1 milligram of theanine or caffeine per dose, respectively. More preferably, the compositions contain less than about 0.5 mg per dose and most preferably less than about 0.1 mg, for example, 0.01 mg or less, preferably 0 mg of theanine and caffeine per dose.

As used herein, a "dose" or "unit dose" or "dose amount" refer to a composition according to the disclosure formulated as a liquid gel capsule, a soft gel capsule tablet, a chewable tablet, a chewable wafer, an extended release formulation, a "gummy" candy, a lozenge, a pastille, chewing gum, an effervescing tablet, and/or liquid formulation (for example about 1 ml to about 30 ml per dose). A dose, unit dose or dose amount may include for example one, two, three, four or five liquid gel capsule, a soft gel capsule tablet, a chewable tablet, a chewable wafer, an extended release formulation, a "gummy" candy, a lozenge, a pastille, chewing gum or an effervescing tablet, and refers to a preferred amount of each ingredient per day. For example, a preferred dose amount of magnesium and *Valerian edulis* for a child is 80 mg and 100 mg, respectively per day and for a teen or adult is 160 mg and 200 mg, respectively, per day. In some embodiments of a two formulation composition, each solid or semi-solid unit (e.g. tablet, softgel, capsule, gummy, etc.) includes 40 mg elemental magnesium and 50 mg dry *Valerian edulis* root and therefore, a dose for a child is two solid or semi-solid units per day while a dose for a teenager or adult is four solid or semi-solid units per day. In a two formulation composition, the liquid formulation includes about 400 IU Vitamin D3 and 500 mg to 1100 mg of a mixture of omega 3 in for example a dose of 1 ml to 5 ml, or about 3 ml.

In alternate embodiments, a dose for a 6 to 10 year old may include for example one, liquid gel capsule, a soft gel capsule tablet, a chewable tablet, a chewable wafer, an extended release formulation, a "gummy" candy, a lozenge, a pastille, chewing gum or an effervescing tablet; a dose for a 11 to 14 year old may include for example two liquid gel capsule, a soft gel capsule tablet, a chewable tablet, a chewable wafer, an extended release formulation, a "gummy" candy, a lozenge, a pastille, chewing gum or an effervescing tablet; and a dose for a teen or adult 15 years old and older may include for example two or three liquid gel capsule, a soft gel capsule tablet, a chewable tablet, a chewable wafer, an extended release formulation, a "gummy" candy, a lozenge, a pastille, chewing gum or an effervescing tablet. For example, a preferred dose amount of magnesium and *Valerian edulis* for a child is 80 mg and 100 mg, respectively per day and for a teen or adult is 160 mg-240 mg and 200 mg-300 mg, respectively, per day. In some embodiments of a two component formulation, each solid or semi-solid unit (e.g. tablet, softgel, capsule, gummy etc.) includes 40 mg elemental magnesium and 50 mg dry *Valerian edulis* root and therefore, a dose for a child is two solid or semi-solid units per day while a dose for a teenager or adult is three, four, five or six solid or semi-solid units per day.

In some embodiments, the composition is formulated as a semi-solid, for example a soft gel capsule and the composition optionally comprises at least one of an oil, a suspending lipid, an emulsifier or a combination thereof as excipient. In some embodiments, the excipient comprises at least one oil and at least one suspending lipid. In some embodiments, excipient comprises at least one oil, at least one suspending lipid and at least one emulsifier.

In some embodiments the at least one oil is selected from soya bean oil, canola (rapeseed) oil, sunflower oil, macadamia oil, peanut oil, grape seed oil, pumpkin seed oil, linseed oil, flaxseed oil, olive oil, maize oil, safflower oil, sesame oil, pine kernel oil, coconut oil, conjugated linoleic acid (CLA), almond oil, peach kernel oil, apricot kernel oil, walnut oil, raspberry seed oil, bilberry seed oil, cranberry seed oil, pomegranate seed oil and other fruit seed oils, sea-buckthorn oil, chia seed oil, *perilla* seed oil, avocado oil, diaglycerol (DAG) or triacylglycerol oil; animal, vegetable or synthetic derived sources of omega 3 fatty acids (e.g. ALA, DHA and EPA), omega 9 fatty acids and combinations thereof.

In some embodiments, the at least one suspending lipid is selected from monoglycerides of fatty acids, diglycerides of fatty acids, bees wax, glyceryl monostearate, glyceryl mono dioleate, fractionated palm oil derivatives, hydrogenated palm fat, hydrogenated soya oil derivatives, vegetable butters, or medium chain triglycerides, and combinations thereof.

In various embodiments the at least one emulsifier is selected from lecithin, polysorbates, or sorbitan monooleates, and combinations thereof.

In some embodiments, the soft gel shell comprises one or more omega-3 fatty acids. In some embodiments, the soft gel shell comprises gelatin or a gelatin substitute and an omega 3 fatty acid or a combination of omega 3 fatty acids such as ALA, DHA and EPA. In some embodiments, the soft gel shell provides the dose of omega 3 fatty acids required in some of the formulations disclosed herein.

According to the methods of the disclosure, the compositions may be administered to a subject to treat ADD/ADHD and related disorders, including amelioration of ADD/ADHD and related symptoms. In a preferred aspect, the compositions are administered in unit dose administered in as a soft gel capsule. In one embodiment, the compositions are administered daily, twice daily, thrice daily, four times daily, up to about 6 times daily.

The compositions in unit dose form may be packaged in bubble packs, boxes, bottles or jars. In one embodiment, two or three servings of the compositions are self-administered by a subject, or are administered by a subject's guardian, per day.

Definitions

It is to be noted that, as used herein, the singular forms "a", "an" and "the" include plural forms unless the content clearly dictates otherwise. Where aspects or embodiments are described in terms of Markush groups or other grouping of alternatives, those skilled in the art will recognize that the invention is also thereby described in terms of any individual member or subgroup of members of the group.

As used herein, the terms "comprising", "including", "having" and grammatical variants thereof are to be taken as specifying the stated features, steps or components but do not preclude the addition of one or more additional features, steps, components or groups thereof.

When a numerical value is preceded by the term "about", the term "about" is intended to indicate +/−10%.

"Treating a subject" refers to administering to the subject a substance effective to ameliorate symptoms associated with a disorder or disease, to lessen the severity of the disorder or disease, to cure the disorder or disease, to slow down the progression of the disorder or disease, or to delay the onset of the disorder or disease. "Treatment" refers to both therapeutic treatment and prophylactic or preventative measures, wherein the object is to prevent a disorder, to delay the onset of the disorder or reduce the symptoms of a disorder. Those in need of treatment include those already experiencing the disease or condition, those prone to having the disease or condition, and those in which the disease or condition is to be prevented. The compounds disclosed herein are administered before, during or subsequent to the onset of the disorder or symptoms.

A "therapeutically effective dose" or "therapeutic dose" or "dose amount" refers to an amount of the compound or component which is effective to achieve an improvement in a subject or his physiological systems including, but not limited to, improved improvement or elimination of symptoms, delayed onset of a disorder, slower progress of symptoms and other indicators selected as appropriate by those skilled in the art.

The terms "ADD/ADHD and related disorders" are meant to encompass ADHD and disorders affecting cognitive, learning, and/or memory functions and the associated symptoms. Included are mild cognitive impairment, attention deficit hyperactivity disorder, anxiety disorder, forgetfulness, impulsivity, mental fatigue, difficulty in concentration and focus.

In a preferred embodiment the subject is a human subject. Children may be treated from the age of about 5 to 12. Adolescents from the age of 12 to about 18, adults from the age of 18 to about 55 and seniors from 55 and older.

Although it may be possible to administer each component of the composition separately, it is preferable to prepare and administer them as a composition, preferably as an orally administered dietary supplement.

As used herein, "extract" refers to an alcoholic extract, an alcohol/water extract or an oil based extract of a material, in particular, a plant component. In some embodiments, provided is a composition comprising *Valerian* (preferably *Valerian officinalis* or *Valerian edulis*) root extract wherein the root extract is crushed desiccated root. In one embodiment, provided herein is a composition comprising Sage oil extract (preferably *Salvia sclarea*; steam extracted and diluted, for example, in grape seed oil) or *Salvia* leaf extract at a dose amount of about 250 mg to 500 mg. In another embodiment, the compositions disclosed herein may further comprising Gingko *biloba* leaf extract (e.g. crushed leaves). In some embodiments, the composition includes a botanical component comprising *Salvia* spp (e.g. *Salvia sclarea*) and *Ginkgo biloba*.

As used herein the term "botanical component" refers to a substance or composition obtained from one or more plant parts, and includes roots, foliage, stems, exudates, metabolites, pigments and the like. Chemical and/or physical methods may be required to obtain the substance or composition from the plant parts. The botanical component may take the form of a solid or a liquid. When the extract is in the liquid form, the extract is also referred to as a tincture. Further provided is a process of preparing a pharmaceutical composition, which comprises: providing one or more compound disclosed herein; and admixing said compound with a pharmaceutically acceptable carrier.

Also provided are kits, containers and formulations that include the compositions provided herein. A kit may include at least one container and at least one label. Suitable containers include, for example, bubble packs, boxes, bottles, vials and tubes. The containers can be formed from a variety of materials such as glass, metal or plastic. A kit may further include a package inserts with indications and/or instructions for use. A preferred kit includes at least two components, a container (about 50 ml to 250 ml) containing a liquid formulation comprising the Vitamin D3; and package or container containing a solid (e.g. tablet or capsule) or semi-solid (e.g. liquid capsule or softgel) component comprising the botanical component and the magnesium, and optionally instructions for use. Accordingly the composition is formulated for oral administration as a liquid in combination with a solid or semi-solid. In one example, per each dose amount of 3 ml, the liquid formulation includes 400 IU Vitamin D3. The liquid formulations optionally further includes a mixture of omega 3 fatty acids, for example a mixture of EPA and DHA in an amount of 500 mg to 1100 mg/dose, preferably about 900 mg/dose, omega 9 in an amount of 100 mg to 500 mg/dose or about 300 mg/dose and optionally one or more antioxidant including Vitamin E, Vitamin C or a derivative thereof. The omega 3 fatty acids may be plant or animal derived or may be synthetic. In some embodiments of the composition, methods and kits, the source of the omega 3 is fish oil. For example a dose of omega 3 and or omega 9 fatty acids may be present in 0.5 to 5 ml, or 2 ml to 4 ml or about 3 ml of fish oil. In one example, each solid or semi-solid unit comprises about 20-100 mg, or about 40 mg elemental Mg; about 20 mg to 100 mg, or about 50 mg *Valerian* spp. dried root, and optionally about 20 mg to 100 mg, or about 50 mg elemental Ca, about 1.0 mcg to 50 mcg, or about 10 mcg elemental Fe and about 0.1 mg to 10 mg, or about 0.5 mg Vitamin B6. The solid or semi-solid unit may further include one or more excipient, binder, plasticizer, edible oil, color agent and the like.

The invention has been described in an illustrative manner, and it is to be understood that the terminology used is intended to be in the nature of words of description rather than of limitation.

Modifications and variations of the present invention are possible in light of the above teachings. It is, therefore, to be understood that within the scope of the appended claims, the invention can be practiced otherwise than as specifically described.

The present invention is illustrated in detail below with reference to examples, but is not to be construed as being limited thereto.

EXAMPLES

Example 1: Botanical Extracts

Clary sage (*Salvia sclarea*) oil extract is preferably prepared by steam distillation of whole plant or flower heads and leaves and dilution in grape seed oil or the like, although there are no limitations to the extraction method. Typically, *Salvia sclarea* oil extract is obtained by steam extraction of the fresh flower heads and leaves. *Salvia sclarea* may also be present in the composition as a dry component, for example finely ground dried *Salvia* leaves (.dbd.dry leaf extract). *Valerian officinalis* or *Valerian edulis* root extract is typically prepared from dried roots that are crushed to a fine powder. There are no limitations to the drying or crushing methods. Some preparations are crushed from roots or other plant parts that are oven-dried with colloidal silicon dioxide as a drying adjuvant.

The tables hereinbelow provide exemplary compositions. It is to be noted that dose amounts may be in the form of a liquid, a combination of a liquid and one or more solid or semi-solid, or one or more solid or semi-solid. For example a dose amount may include 1-5 ml of a liquid formulation and 1-3 tablets, capsules soft gels etc. Furthermore, throughout the application, the dose amounts of minerals, including magnesium, calcium and iron, as presented as elemental mineral amounts ("*" in the tables below).

Example 2: Composition for Children/Adolescents

Table 2A provides an exemplary formulation useful in the treatment of ADHD and related disorders in children and adolescents.

TABLE 2A

Dose amounts for children and adolescents

| Component | Type | Range | Preferred Form |
|---|---|---|---|
| Magnesium | mineral | 50 mg-500 mg* | Magnesium citrate |
| Vitamin D3 | vitamin | 50 IU-1000 IU | Cholecalciferol |
| *Valerian* | botanical | 20 mg-500 mg | *Valerian officinalis/edulis* dry root |

TABLE 2A-continued

Dose amounts for children and adolescents

| Component | Type | Range | Preferred Form |
|---|---|---|---|
| Excipients | Pectin, gelatin, and/or polyol | | Gummy formulation or pastille |
| Colorant, flavors | To suit | | |

Table 2B provides an exemplary formulation useful in the treatment of ADHD and related disorders in children and adolescents.

TABLE 2B

Dose amounts for children and adolescents

| Component | Type | Range | Preferred Form |
|---|---|---|---|
| Magnesium | mineral | 50 mg-500 mg* | Magnesium citrate |
| Vitamin D3 | vitamin | 50 IU-1000 IU | Cholecalciferol |
| *Valerian* | botanical | 20 mg-500 mg | *Valerian officinalis/edulis* dry root |
| Iron | mineral | 10 mcg-100 mcg* | Iron fumarate/bisglycinate |
| Calcium | mineral | 50 mg-500 mg* | Calcium carbonate |
| Vitamin B6 | vitamin | 1-5 mg | Pyridoxine hydrochloride |
| Omega 3 | fatty acid | 100 mg-1100 mg | ALA, EPA, DHA or combination |
| Excipients | Pectin, gelatin and/or polyol | | Gummy formulation or pastille |
| Colorant, flavors | To suit | | |

Preferred formulations for children and adolescents are pharmaceutical confectionaries, including "gummies", lozenges, pastilles and chewing gum. A preferred dose for children to the age of 12 is two gels, lozenges, etc. per day, for adolescents up to the age of 18, three gels or lozenges per day.

Table 2C provides an exemplary formulation useful in the treatment of ADHD and related disorders in children and adolescents, in the form of a soft gel, for example a chewable or swallowable soft gel.

TABLE 2C

Dose amounts for children and adolescents

| Component | Type | Range | Preferred Form |
|---|---|---|---|
| Magnesium | mineral | 50 mg-500 mg* | Magnesium citrate |
| Vitamin D3 | vitamin | 50 IU-1000 IU | Cholecalciferol |
| *Valerian* | botanical | 20 mg-500 mg | *Valerian officinalis/edulis* dry root |
| Iron | mineral | 10 mcg-100 mcg* | Iron fumarate or bisglycinate |
| Calcium | mineral | 50 mg-500 mg* | Calcium carbonate |
| Vitamin B6 | vitamin | 1-5 mg | Pyridoxine hydrochloride |
| Excipients | lipid | | |
| Colorant, flavors | Optional, to suit | | |
| Shell | Gelatin/substitute | 100 mg-500 mg | Soft gel shell with Omega 3 fatty acid(s) |

Example 3: Composition for Adults and Seniors

Table 3A provides an exemplary formulation useful in the treatment of ADHD and related disorders in adults and seniors.

TABLE 3A

Dose amounts for adults and seniors
Preferred Component Type Range Form

| Component | Type | Range | Preferred Form |
|---|---|---|---|
| Magnesium | mineral | 50 mg-500 mg* | Magnesium citrate |
| Vitamin D3 | vitamin | 50 IU-1000 IU | Cholecalciferol |
| Sage | botanical | 10 microL-250 microL (oil)/ 250 mg-500 mg (dry) | *Salvia sclarea* extract oil or dry leaf |
| Excipients | lipidic | | Capsule, tablet or Soft gel |

Table 3B provides an exemplary formulation useful in the treatment of ADHD and related disorders in adults and seniors.

TABLE 3B

Dose amounts for adults and seniors

| Component | Type | Range | Preferred Form |
|---|---|---|---|
| Magnesium | mineral | 50 mg-500 mg* | Magnesium citrate |
| Vitamin D3 | vitamin | 50 IU-1000 IU | Cholecalciferol |
| Sage | botanical | 10 microL-250 microL (oil)/ 250 mg-500 mg (dry) | *Salvia sclarea* oil extract or dry leaf |
| Iron | mineral | 10 mcg-100 mcg* | Iron fumarate/bisglycinate |
| Calcium | mineral | 50 mg-500 mg* | Calcium carbonate |
| Vitamin B6 | vitamin | 1 mg-5 mg | Pyridoxine hydrochloride |
| Omega 3 | fatty acid | 100 mg-1100 mg | ALA, EPA, DHA or combination |
| *Gingko biloba* | Botanical | 10 mg-200 mg | Leaf extract |
| Excipients | lipidic | | Capsule, tablet or Soft gel |

Table 3C provides an exemplary formulation useful in the treatment of ADHD and related disorders in adults and seniors in the form of a soft gel.

TABLE 3C

Dose amounts for adults and seniors

| Component | Type | Range | Preferred Form |
|---|---|---|---|
| Magnesium | mineral | 50 mg-500 mg* | Magnesium citrate |
| Vitamin D3 | vitamin | 50 IU-1000 IU | Cholecalciferol |
| Sage | botanical | 10 microL-250 microL (oil)/ 250 mg-500 mg (dry) | *Salvia sclarea* oil extract/dry leaf |
| Iron | mineral | 10 mcg-100 mcg* | Iron fumarate/bisglycinate |
| Calcium | mineral | 50 mg-500 mg* | Calcium carbonate |
| Vitamin B6 | vitamin | 1 mg-5 mg | Pyridoxine hydrochloride |
| *Gingko biloba* | botanical | 10 mg-200 mg | Leaf extract |
| Excipients | lipidic | | Soft gel |
| Shell | Gelatin/gelatin substitute | | Soft gel shell including Omega 3 fatty acid(s) |

The above formulation may be prepared as a tablet, capsule, softgel etc., as described herein. A preferred formulation is a capsule or a softgel. Softgels are prepared, for example, by utilizing the softgel technology, known as the R P Scherer soft gel technology, or other methods known in the art. The shell of the soft gel may comprise gelatin (animal or vegetarian) or a gelatin substitute such as starch and/or carrageenan.

Preferred dose for adults 18-55 and seniors 55+ up is two to three tablets, capsules or two to three softgels per day.

Example 4: Two Formulation Composition

Table 4A provides an exemplary composition (two formulations) useful in the treatment of ADHD and related disorders in children, adolescents and adults as a two component formulation, for example a liquid formulation and a tablet, capsule or chewable or swallowable soft gel.

TABLE 4A amounts per formulation

| | Type | Range | Preferred | Preferred Form |
|---|---|---|---|---|
| Solid or semisolid unit | | | | |
| Magnesium | mineral | 10 mg-100 mg | 40 mg* | Magnesium citrate |
| Valerian | botanical | 20 mg-500 mg | 50 mg | Valerian edulis dry root extract |
| Iron | mineral | 10 mcg-50 mcg | 10 mcg* | Iron bisglycinate |
| Calcium | mineral | 10 mg-500 mg | 50 mg* | Calcium carbonate |
| Vitamin B6 | vitamin | 1 mg-5 mg | 0.5 mg | Pyridoxine hydrochloride |
| Colorant, flavors, preservatives | Optional, to suit | | | |
| Liquid formulation | | | | |
| Vitamin D3 | vitamin | 50 IU-1000 IU | 400 IU | Cholecalciferol |
| Vitamin E | Vitamin | 0.1-10 mg | 0.75 mg | tocopherol |
| Omega 3 | Fatty acid | 500 to 1100 mg | 1020 mg | EPA and DHA |
| Omega 9 | Fatty acid | 100-500 mg | 300 mg | |
| Colorant, flavors, preservatives | Optional, to suit | | 0.015 ml soy lecithin 0.003 ml ascorbyl | Soy lecithin, ascorbyl palmitate, Lemon flavoring |

A preferred dose amount for a child is 3 ml of the liquid formulation and 2 solid/semi-solid units once a day (total of 80 mg elemental Mg; 100 mg *Valerian edulis* (dry root extract); 20 mcg elemental iron; 100 mg elemental Ca; 1 mg vitamin B6). A preferred dose amount for a teenager or adult is 3 ml of the liquid formulation once a day and 2-4 solid/semi-solid units once (2-4 units) or twice a day (1-2 units twice a day) (total 80 mg-160 mg elemental Mg; 100 mg-200 mg *Valerian edulis* (dry root extract); 20 mcg-40 mcg elemental iron; 100 mg-200 mg elemental Ca; 1.0 mg-2.0 mg vitamin B6).

In an alternative embodiment, a composition for an adult (over about age 20) and senior suffering from, for example lack of focus, forgetfulness and/or disorganization in the absence of hyperactivity, the botanical component is preferably *Salvia* spp and *Ginkgo biloba*. Table 4B provides an example of such a two component formulation.

TABLE 4B amounts per component for adults over the age of about 20 years

| | Type | Range | Preferred | Preferred Form |
|---|---|---|---|---|
| Solid or semisolid unit | | | | |
| Magnesium | mineral | 10 mg-100 mg | 40 mg* | Magnesium citrate |
| Ginkgo biloba | botanical | 10 mg-200 mg | 20 mg-50 mg | Ginkgo dry root extract |
| Iron | mineral | 10 mcg-50 mcg | 10 mcg* | Iron bisglycinate |
| Calcium | mineral | 10 mg-500 mg | 50 mg* | Calcium carbonate |
| Vitamin B6 | vitamin | 1 mg-5 mg | 0.5 mg | Pyridoxine hydrochloride |
| Sage (e.g. if absent in liquid) | botanical | 50 mg-1000 mg | 120 mg-250 mg | Salvia sclarea dry leaf extract |
| Colorant, flavors, preservatives | Optional, to suit | | | |
| Liquid formulation | | | | |
| Sage (e.g. if absent from above) | botanical | 10 microL-250 microL | 10 uL | Salvia sclarea oil extract |
| Vitamin D3 | vitamin | 50 IU-1000 IU | 400 IU | Cholecalciferol |
| Vitamin E | Vitamin | 0.1-10 mg | 0.75 mg | tocopherol |
| Omega 3 | Fatty acid | 500 to 1100 mg | 1020 mg | EPA and DHA (and others) |
| Omega 9 | Fatty acid | 100-500 mg | 300 mg | |
| Colorant, flavors, preservatives | Optional, to suit | | 0.015 ml soy lecithin 0.003 ml ascorbyl | Soy lecithin, ascorbyl palmitate, Lemon flavoring |

A preferred dose amount for an adult over the age about 20 and seniors is 3 ml of the liquid formulation and 2 solid/semi-solid units taken once or twice a day (total of 80 mg-160 mg elemental Mg; 250 mg *Salvia sclarea* (dry leaf extract) 20 mg-80 mg *Ginkgo biloba* (dry leaf extract); 20 mcg-40 mcg elemental iron; 100 mg-200 mg elemental Ca; 1 mg-2 mg vitamin B6). In some embodiments, the liquid formulation may include one or more of the botanical components.

Preferably the composition is packaged in a kit, whereby the liquid formulation is present in a bottle or vial of from about 50 ml to about 250 ml, or about 90 ml to 120 ml; and the solid or semi-solid unit is present in a bottle or push packets. The kit may further include a measuring device such as a syringe or measuring cup. In some embodiments, the liquid formulation and/or the solid or semi-solid units (e.g. tablet, softgel, capsule) may be present in a container with a child proof cap.

Example 5: Clinical Evaluation

The compositions (liquid, solid and or semi-solid) disclosed hereinabove are tested in human subjects, children, adolescents and or adults, having a desire or need to improve concentration, focus, attention span and the like.

Soldiers between the ages of 18 and 25 in a high stress combat unit who were given the two component formulation (3 ml liquid formulation and four capsules) daily for two weeks felt a significant improvement in their alertness and ability to focus on the mission.

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

I claim:

1. A method for treating attention deficit hyperactivity disorder in a human in need thereof, consisting essentially of administering to the human in need thereof therapeutically effective amounts of magnesium; vitamin D3; gingko biloba extract; and a botanical component selected from the group consisting of *Valerian officinalis* and *Valerian edulis*, to effectively treat the attention deficit hyperactivity disorder in the human in need thereof.

2. The method of claim 1, wherein the magnesium is present in a dose amount of 50 mg to 500 mg (elemental Mg), and wherein the vitamin D3 is present in a dose amount of 50 IU to 1000 IU.

3. The method of claim 1, wherein the magnesium is present in a dose amount of about 80 mg to 160 mg (elemental Mg), and wherein the vitamin D3 is present in a dose amount of about 200 IU to 400 IU.

4. The method of claim 1, wherein the botanical component is present in a root extract at a dose amount of 20 mg to 500 mg.

5. The method of claim 1, further consisting essentially of administering to the human in need thereof a therapeutically effective amount of at least one component selected from the group consisting of iron, calcium, an omega 3 fatty acid, and a mixture of omega 3 fatty acids, an omega 9 fatty acid, vitamin E, and vitamin B6.

6. The method of claim 5, wherein the iron is present in a dose amount of 10 microgram to 100 microgram, or 20 microgram to 40 microgram (elemental Fe).

7. The method of claim 5, wherein the calcium is present in a dose amount of 50 mg to 500 mg, or 100 mg to 200 mg (elemental Ca).

8. The method of claim 5, wherein the omega 3 fatty acid or mixture of omega 3 fatty acids is present at a dose amount of 100 mg to 1100 mg.

9. The method of claim 5, wherein the vitamin B6 is present (as pyroxidine hydrochloride) is present at a dose amount of 0.1 mg to 20 mg, or 1.0 mg to 2.0 mg.

10. The method of claim 1, wherein the gingko *biloba* is present as a leaf extract at a dose amount of 10 mg to 200 mg.

11. The method of claim 1, wherein the magnesium; vitamin D3; gingko *biloba*; and botanical component are formulated together in a form selected from the group consisting of liquid capsule, a soft gel capsule, a tablet, a chewable tablet, a chewable wafer, a gummy candy, a lozenge, a pastilles, chewing gum, and an effervescing tablet.

12. The method of claim 1, wherein the Vitamin D3 is administered at about 400 IU per dose.

13. The method of claim 12, further consisting essentially of administering about 0.75 mg Vitamin E, about 500 mg to 1100 mg omega 3 fatty acids and about 300 mg omega 9 fatty acid per dose.

14. A method for treating attention deficit hyperactivity disorder in a human in need thereof, consisting essentially of administering to the human in need thereof: magnesium (as magnesium citrate) in a dose amount of about 80 mg to 160 mg (elemental Mg), vitamin D3 in a dose amount of about 200-400 IU; *Valerian* officinal or *Valerian edulis* root extract in a dose amount of about 20 mg to 500 mg; iron (as iron fumarate or iron bisglycinate) in a dose amount of about 20 micrograms to 40 micrograms (elemental Fe), calcium (as calcium carbonate) in a dose amount of about 100 mg to 200 mg (elemental Ca), a mixture of omega 3 fatty acids in a dose amount of about 500 mg to 1100 mg, vitamin B6 (as pyridoxine hydrochloride) in a dose amount of about 1.0 mg to 2.0 mg, and gingko *biloba* as a leaf extract at a dose amount of about 80 mg, to effectively treat the attention deficit hyperactivity disorder in the human in need thereof.

* * * * *